United States Patent [19]

Manosalva et al.

[11] Patent Number: 5,341,823
[45] Date of Patent: Aug. 30, 1994

[54] METHOD FOR LOADING A T-SHAPED TENSION DEVICE INTO A SLOTTED NEEDLE

[75] Inventors: Edgar G. Manosalva, Columbus; Jeffrey R. Ross, Dublin; Donald J. Goldhardt, Grove City, all of Ohio

[73] Assignee: Abbott Laboratories, Abbott Park, Ill.

[21] Appl. No.: 148,228

[22] Filed: Nov. 8, 1993

Related U.S. Application Data

[62] Division of Ser. No. 38,751, Mar. 26, 1993, Pat. No. 5,307,924.

[51] Int. Cl.$^5$ .................... A61B 19/00; A61M 31/00
[52] U.S. Cl. ........................ 128/898; 604/51; 606/215
[58] Field of Search ................ 128/897-99; 604/51, 264, 272; 600/37; 606/108, 215, 220

[56] References Cited

U.S. PATENT DOCUMENTS

| | | | |
|---|---|---|---|
| Re. 34,021 | 8/1992 | Mueller et al. | 604/51 |
| 2,747,574 | 5/1956 | Lorenzo | 206/370 |
| 3,696,920 | 10/1972 | Lahay | 206/370 |
| 3,779,375 | 12/1973 | Foster | 206/63.3 |
| 4,391,365 | 7/1983 | Batchelor | 206/485 |
| 4,572,363 | 2/1986 | Alpern | 206/63.3 |
| 4,807,752 | 2/1989 | Chodrow | 206/485 |
| 4,946,035 | 8/1990 | Grimm et al. | 206/370 |
| 5,047,019 | 9/1991 | Sincock | 206/486 |
| 5,062,526 | 11/1991 | Rudnick et al. | 206/486 |
| 5,099,992 | 2/1992 | Heimreid | 206/370 |
| 5,123,528 | 6/1992 | Brown et al. | 206/63.3 |
| 5,151,086 | 9/1992 | Duh et al. | 604/51 |

*Primary Examiner*—Lee S. Cohen
*Assistant Examiner*—Lee S. Lacyk
*Attorney, Agent, or Firm*—Lonnie R. Drayer; Donald O. Nickey

[57] ABSTRACT

A T-fastener installation kit includes a packaging device for loading the T-fastener into a slotted needle without requiring the hands of the surgeon to touch the sharp end of the needle. T-fasteners may be commonly used, for example, in surgical procedures in which the T-fasteners are used to secure a patient's stomach or bowel in apposition to the abdominal wall. The packaging device includes a housing having a cylindrical recess into which the "T" head of the T-fastener is loaded. The surgeon can slide the open end of the slotted needle into the cylindrical recess and over the "T" head of the T-fastener, thereby effectively loading the T-fastener into the slotted needle without requiring the surgeon to touch the sharp point of the needle.

1 Claim, 10 Drawing Sheets

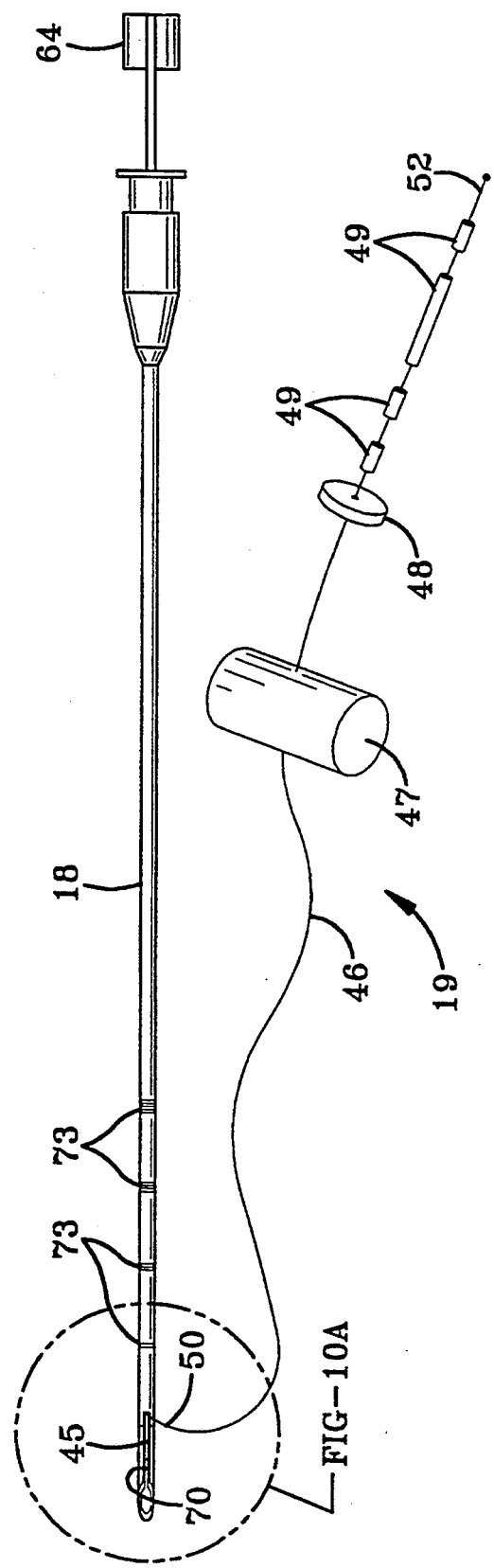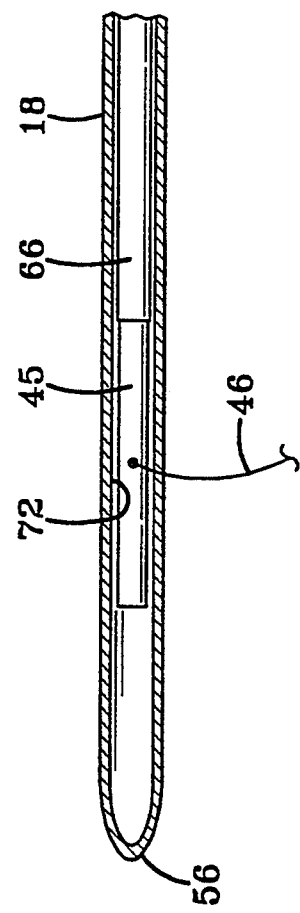

METHOD FOR LOADING A T-SHAPED TENSION DEVICE INTO A SLOTTED NEEDLE

This is a division of application Ser. No. 08/038,751 filed on Mar. 26, 1993 now U.S. Pat. No. 5,307,924.

BACKGROUND OF THE INVENTION

1. Field of Invention

The present invention relates to surgical instruments, and more particularly to T-shaped tension members used in surgical procedures, and even more particularly to a device for packaging these T-shaped tension members and loading them into a slotted needle without requiring a person's hands to handle or come near the sharp end of the slotted needle.

2. Description of the Related Art

U.S. Pat. Re. No. 34,021 discloses a method and apparatus for fixing a hollow organ of a living body to a body wall using T-shaped tension members (hereinafter referred to as T-fasteners). Examples of surgical procedures which may utilize the teachings of U.S. Pat. Re. No. 34,021 are securing a patient's stomach or bowel in apposition to the abdominal wall, such as as in a gastrostomy or jejunostomy procedure. These procedures are performed to facilitate the insertion of a feeding tube through the abdominal wall directly into the stomach or bowel. Examples of individuals who may require such a procedure includes burn patients, whose daily caloric needs are very high; critically ill, weak or comatose patients who may be unable to swallow food; and patients suffering from a diseased or traumatized esophagus, who may be unable to swallow food. Increasingly, a new class of persons requiring such treatment include patients infected with the HIV virus.

A relatively new method of placing a gastrostomy tube or jejunostomy tube is described in U.S. Pat. No. 5,151,086. In this patent, a laparoscopic procedure is described which utilizes instruments and equipment which passes through the skin and surrounding tissue to the surgical site. The laparoscopic procedures require the use of many instruments and supplies including a nasogastric tube, scalpel, needles, syringes, T-fasteners, a J-guide wire, dilators, a gastrostomy tube, stylet, and water-soluble lubricant.

In the procedure to be described later herein, a "T" head of a T-fastener is inserted into a slotted needle. Because several T-fasteners may be installed during a surgical procedure with the same needle, it is required that a surgeon, or an assistant, repeatedly load T-fasteners into the needle. The risk of a surgeon, or an assistant, inadvertently pricking his finger(s), and thereby enhancing the possibility of transmitting a disease between a member of the surgical team and the patient, or vice versa, with a needle can be reduced by the method and apparatus for loading the T-fastener assemblies into the slotted needle disclosed herein. The method and apparatus of the present invention allow a "T" head of a T-fastener to be loaded into a slotted needle without the surgeon, or an assistant, having to touch the slotted needle near its point, thus reducing the chance of inadvertently pricking his finger.

BRIEF DESCRIPTION OF THE DRAWINGS

The features of the present invention which are believed to be novel or set forth with particularity in the appended claims. The present invention, both as to its structure and manner of operation, may best be understood by referring to the following detailed description, taken in accordance with the accompanying drawings in which:

FIG. 10 illustrates a T-fastener which has been loaded into a slotted needle, ready for installation into a patient; and FIG. 10A is an enlarged view of a portion of FIG. 10, partially broken away.

DETAILED DESCRIPTION OF THE PREFERRED EMBODIMENT OF THE INVENTION

DESCRIPTION OF APPARATUS

Figure 1:
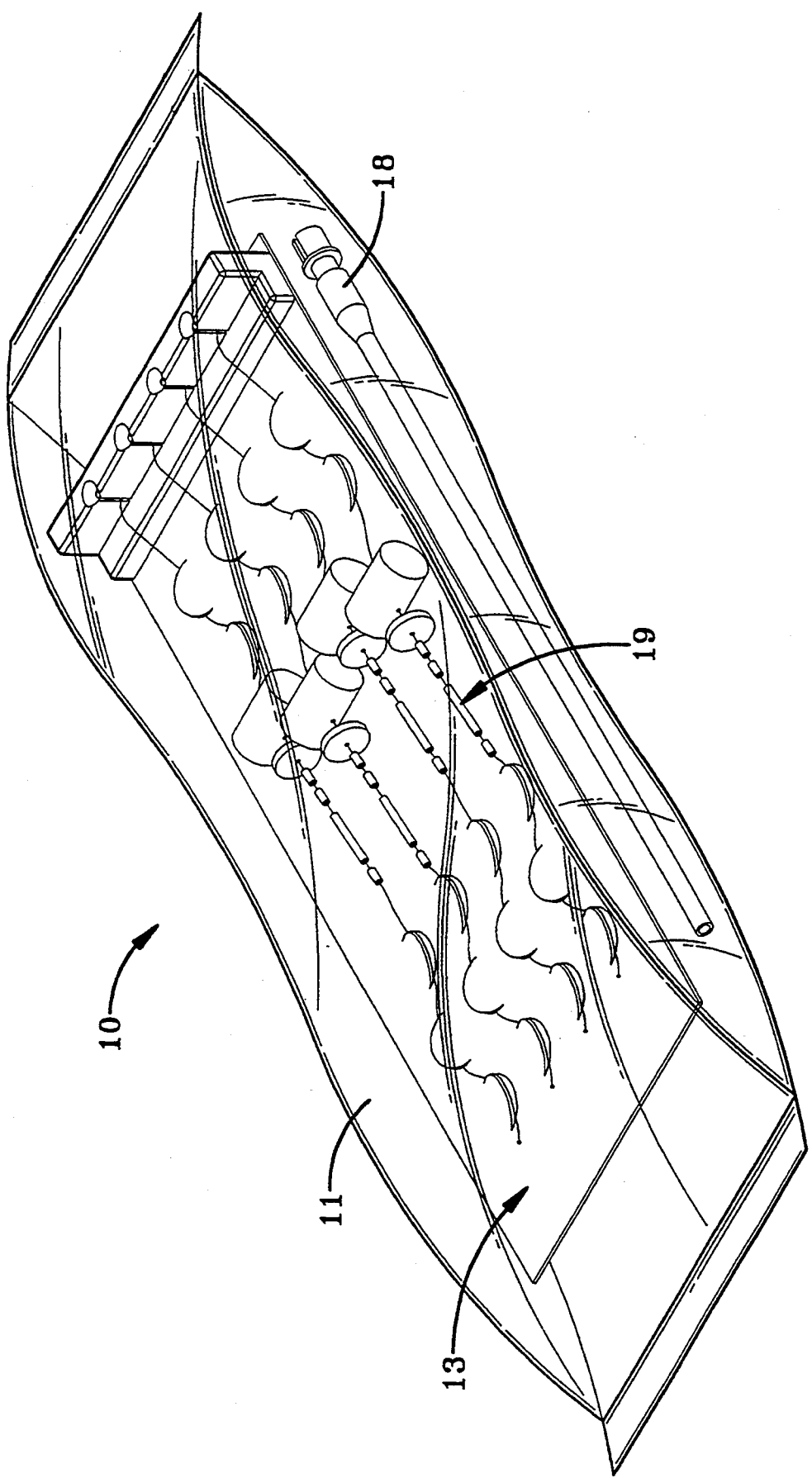
FIG. 1 is a perspective view of an unopened T-fastener installation kit of the present invention.

With reference to FIG. 1, there is shown a T-fastener installation kit 10 which is enclosed within a sealed clear plastic wrapper 11. The wrapper 11 encloses a packaging device 13, which contains plurality of T-fasteners 19, and a slotted needle 18 which is necessary for installing the T-fasteners 19. It is understood that the wrapper 11 may comprise any suitable material that is capable of surviving a sterilization procedure, such as high temperatures or ethylene oxide, and may be either transparent or opaque.

Figure 2:
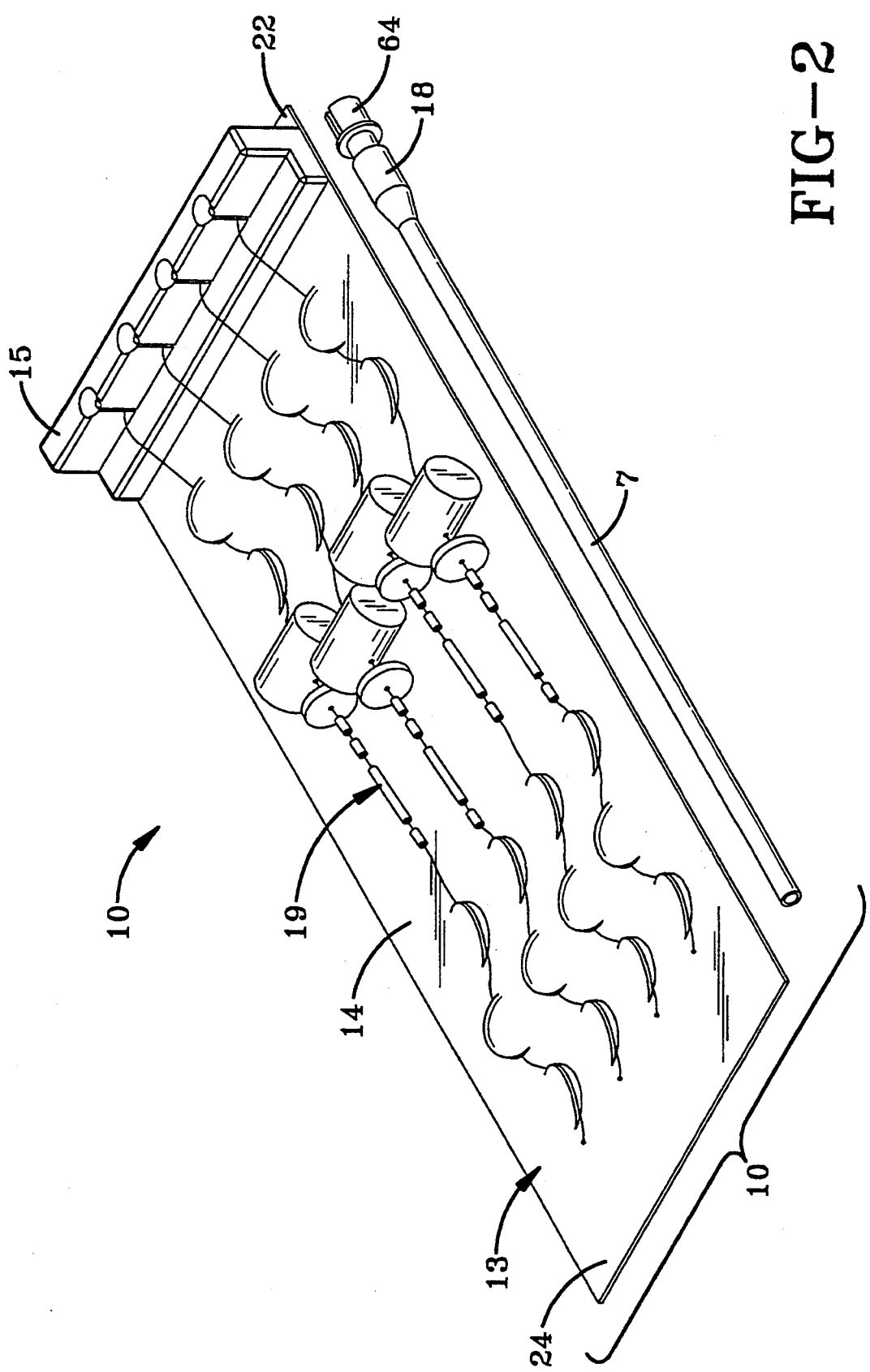
FIG. 2 is a perspective view of the T-fastener installation kit of FIG. 1 with the outer wrapping removed, showing that the kit comprises a packaging device, T-fasteners and a slotted needle within a protective sleeve.
Figure 3:
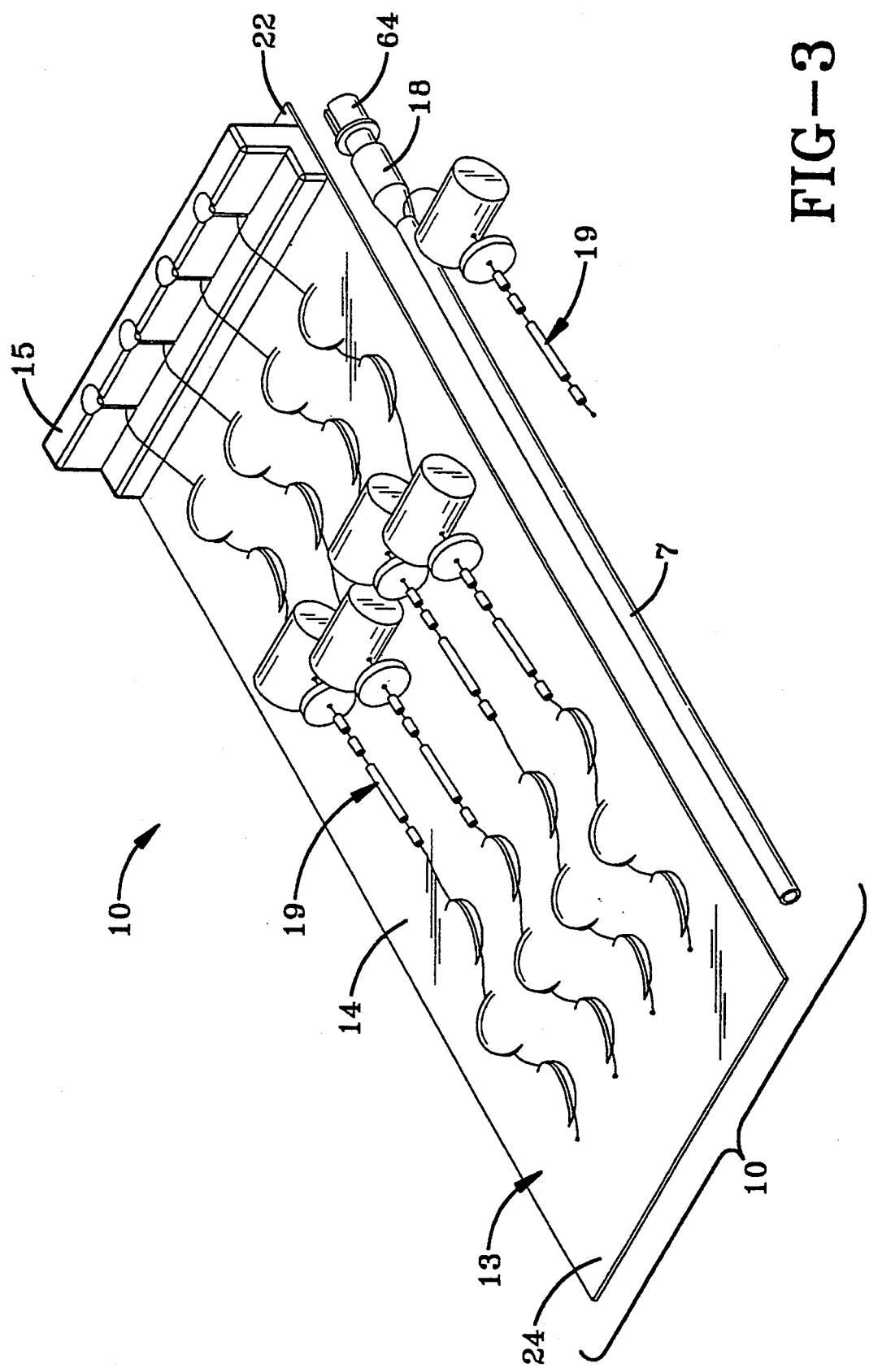
FIG. 3 is a perspective view of a T-fastener installation kit of an alternative embodiment with the outer wrapping removed, having a T-fastener pre-loaded in the slotted needle.

With reference to FIG. 2, the T-fastener installation kit 10 is shown with the plastic wrapper removed. It can be seen that a preferred embodiment of a kit 10 comprises the packaging device 13, a plurality of T-fasteners 19, preferably at least four, and a slotted needle 18 having a shaft portion which is disposed within a protective sheath 7. A stylet 64 is provided in assembly with the slotted needle 18 such that a portion of the stylet is disposed within the bore of the slotted needle. Although four T-fasteners 19 are generally used in a surgical procedure it is preferred, as shown in FIG. 3, that an extra T-fastener 19 be included in the T-fastener installation kit 10 in case a T-fastener 19 is broken, dropped, or otherwise becomes unusable during the surgical procedure. While the fifth T-fastener is shown preloaded into the slotted needle, with a protective sheath 7 over the shaft of the needle, it is understood that the packaging device 13, could be adapted to accommodate five T-fastener assemblies, or in fact any desired number of T-fastener assemblies.

With reference to the embodiments of both FIGS. 2 and 3, the packaging device 13 comprises a substantially planar base 14 and a housing 15. The base 14 has a first end 22 and a second end 24. The housing 15 is fixedly attached to the base 14 in close proximity to the first end 22 of the base. In a currently preferred embodiment, the base 14 is made of cardboard while the housing 15 is made of a plastic material such as a polycarbonate. It is understood that any suitable material, or materials, may be employed in the packaging device and that the base and housing may be molded integrally, or made separately and then attached to one another by suitable means for attachment such as an adhesive, tabs and slots, or mechanical fasteners.

Figure 4:
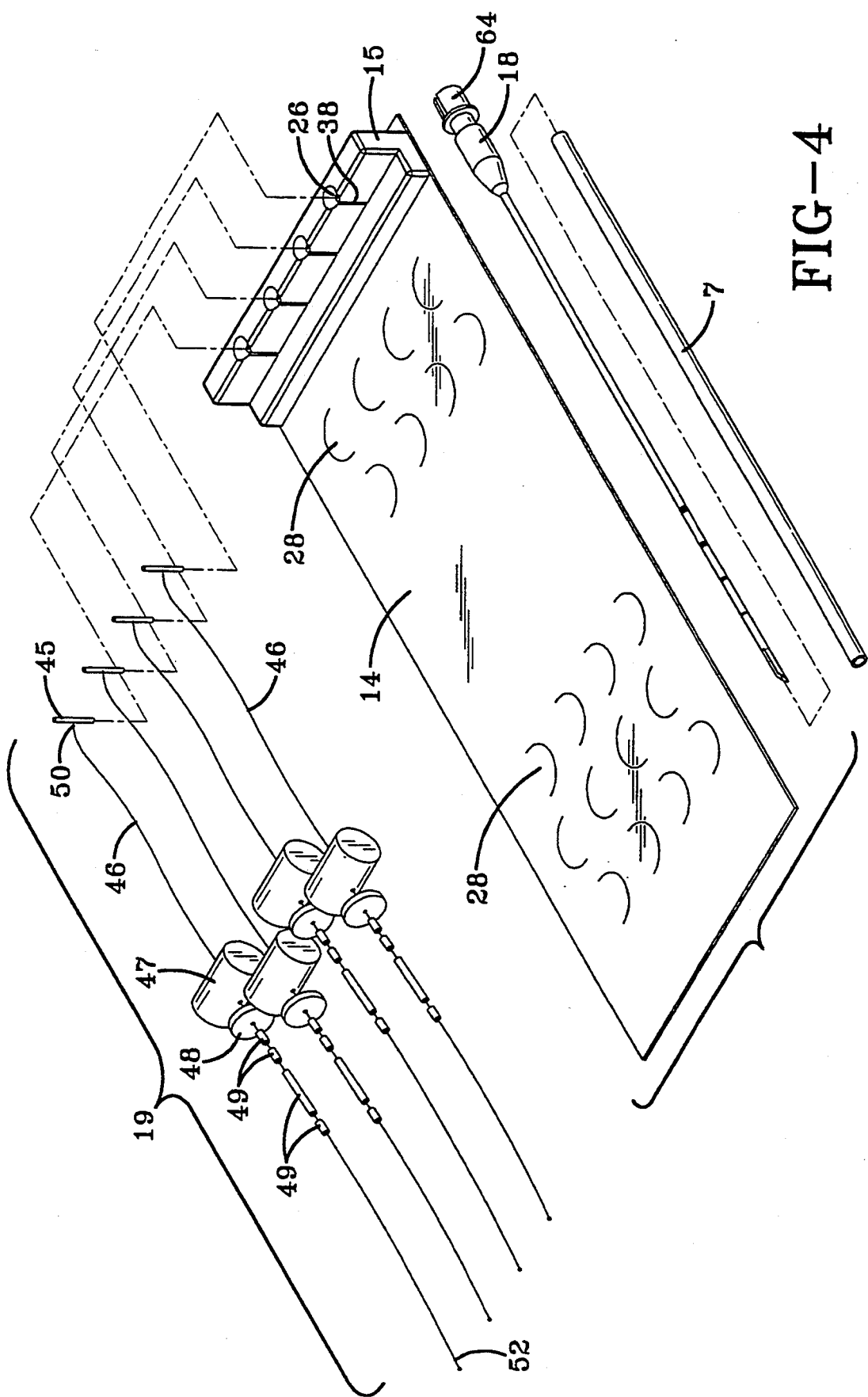
FIG. 4 is an exploded view of the contents of the packaging device, showing the T-fasteners and their relation to the packaging device.

With reference to FIGS. 4 and 10, the components of a T-fastener 19 will be described. Each T-fastener 19 comprises a "T" head 45 and a suture 46. The suture 46 has a first end 50, at which end the "T" head 45 is located, and a second end 52. Threaded onto the suture 46 is a compressible pledget 47, a retention disk or washer 48 and one or more crimpable clamping elements 49. The "T" head 45 is preferably an elongated stainless steel cylinder, which is affixed to one end 50 of a suture 46, which is preferably formed of nylon. The pledget 47 is preferably formed of a soft, absorbent material such as cotton or methylcellulose, and acts as a cushion against the skin and as an absorbent for fluids. The compression applying tension disk or washer 48 is preferably formed of nylon, and the crimpable clamping devices 19 are preferably formed of aluminum. It is understood that the exact components of a T-fastener may be varied in terms of materials and configurations. Therefore, as used herein and in the claims a "T-fastener" is understood to be a percutaneous fixation device suitable to fix the position of a hollow organ within a body, comprising: a "T" head comprising a stiff member, an elongated, relatively more flexible primary tension filament secured at the mid-region of said "T" head, said elongated primary tension filament having a free end trailing back from said "T" head, and compressible means threaded on said elongated primary tension filament for bearing in a cushioning manner with compression against the skin of the body, and means for pressing upon said compressible means while clamping said primary tension member to apply tension to said primary tension filament to draw said "T" head against the inner surface of the hollow organ.

With reference to FIGS. 4, 10 and 10A the slotted needle 18 has a sharp beveled tip 56, a longitudinal slot 70 associated with the tip, a length suitable to permit percutaneous insertion, and has a bore 72 therethrough with a diameter large enough to accept a "T" head 45 so that the "T" head is entirely within the needle when the needle is thrust through flesh into the interior of a hollow organ. The longitudinal slot 70 extends parallel to the longitudinal axis of the bore which extends through the entire length of the slotted needle.

Also, as shown, the slotted needle has indicia 73 located on its outer surface to indicate the depth of insertion of the needle. A stylet 64 is disposed within the bore 72 of the needle, and when a T-fastener is loaded in the needle (FIG. 10A) one end 66 of the stylet is near or touching the "T" head and the other end of the stylet extends through the hub of the slotted needle.

With reference to FIG. 4, the T-fasteners 19 are shown, ready to be loaded into the packaging device 13. The "T" heads 45 of the T-fasteners 19 are oriented perpendicularly to the sutures 46, as is their normal, relaxed position. The "T" heads 45 are inserted into cylindrical recesses 26 in the housing 15. Each suture 46 is extended through a notch 38 in the housing and threaded under cutouts 28 in the base 14. The cutouts 28 are generally semicircular perforations in the base 14 which can be selectively elastically deformed outwardly from the base 14 to receive and retain the sutures 46. The T-fasteners 19 assembled with the packaging device 13 are shown in FIGS. 2 and 3.

Figure 5:
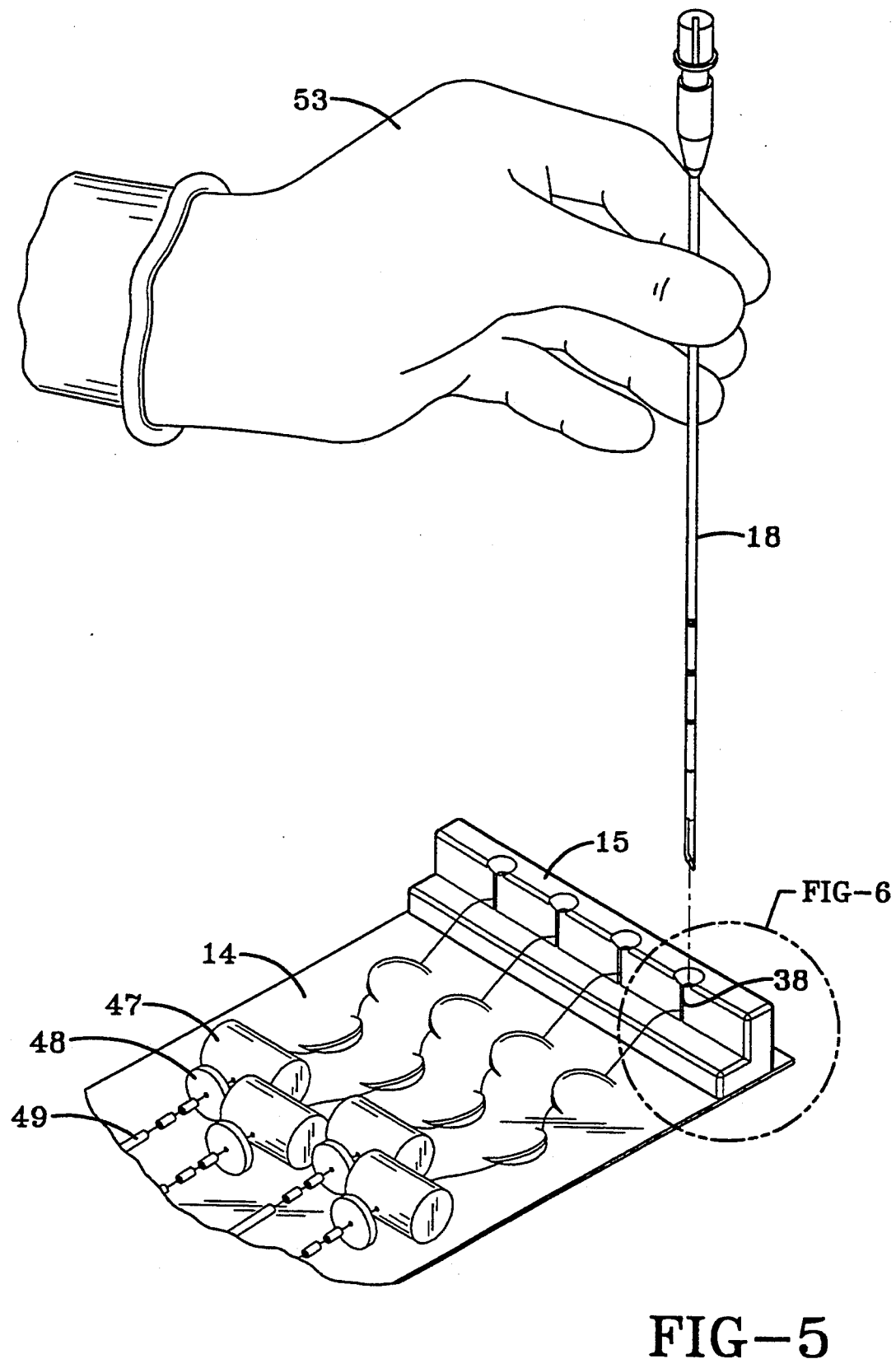
FIG. 5 illustrates the procedure whereby a "T" head of a T-fastener can be loaded into the pointed end of a slotted needle.
Figure 6:
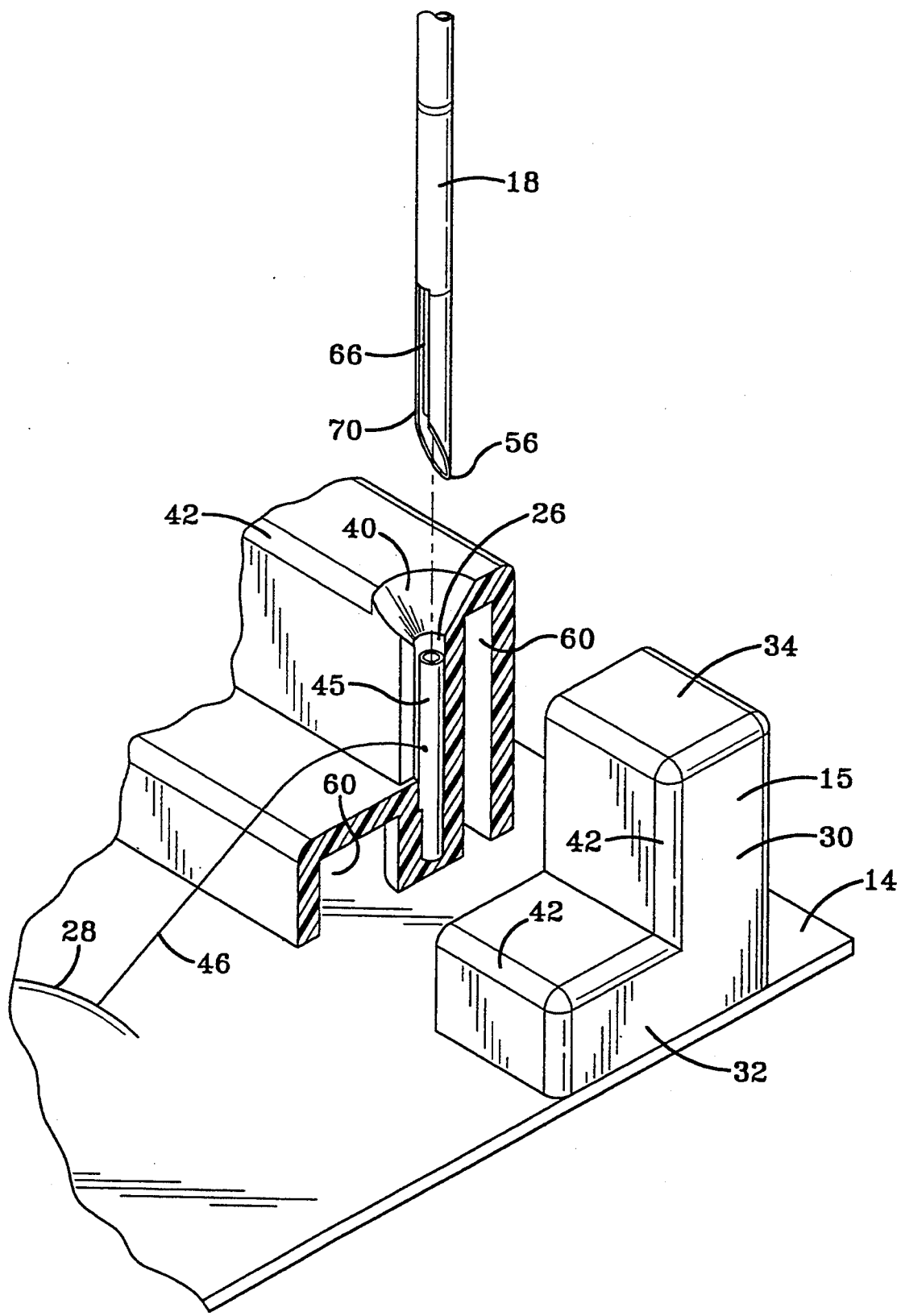
FIG. 6 is a enlarged view of a portion of FIG. 5, showing the orientation of the "T" head of the T-fastener within the loading device of the invention.

With reference to FIGS. 5 and 6, the innovative housing 15 will be described. In a currently preferred embodiment, the housing 15 comprises in a vertical cross-section a first generally rectangular section 30 which is coupled to a second generally rectangular section 32 to form a "step" shaped or "L" shaped configuration. In other embodiments, it is foreseeable that the second rectangular section 32 would be unnecessary and might be eliminated as a cost reduction measure. As used herein and in the claims, terms such as "vertical", "horizontal", "upper", "lower", "top", and "bottom" are understood to refer to a packaging device 13 having its substantially planar base 14 resting on a flat horizontal surface such that the housing 15 extends upwardly with respect to said flat horizontal surface. A top surface 34 of the housing 15 features cylindrically-shaped recesses 26 which extend vertically into the housing 15. That is to say, the housing 15 has cylindrically-shaped wells 26 therein which are open at the top surface 34 of the housing. Each of these cylindrical recesses 26 has an inside diameter which is slightly larger than the outside diameter of the "T" heads 45 of the T-fasteners 19. With regard to both the cylindrical recesses 26 and the "T" heads 45, the respective diameters are measured across the smallest dimension of the item, as is usual.

As can be seen most clearly in FIG. 5, a notch 38 in the housing 15 communicates with the cylindrical recess 26. The notch 38 is generally parallel to the longitudinal axis of the cylindrical recess 26. When the "T" head 45 of a T-fastener 19 is correctly loaded into the housing 15, the T-fastener suture 46 extends through a notch 38. In the preferred embodiment, as can be seen most clearly in FIG. 6, the top surface 34 of the housing 15 features a bevelled portion 40 encircling each cylindrical recess 26 to assist a surgeon, or his assistant, in directing the sharp end 56 of the slotted needle 18 into the cylindrical recess 26. The outer surfaces of the housing 15 preferably have rounded corners 42. One of the advantages of such rounded corners 42 is a reduction in the possibility of a sharp corner piercing the wrapper and contaminating the contents of the T-fastener kit 10.

In a preferred embodiment the housing 15 features hollow areas 60 on its underside. These hollow areas 60 strengthen the structural rigidity of the housing 15 while also contributing to weight and material savings. The second rectangular section 32 performs the function of lifting the suture 46 above the surface of the base 14. Because the surgeon or assistant will undoubtedly be wearing latex gloves, this lifting of the suture 46 assists in removing a suture 46 from the base 14 and cutouts 28. A finger can be slipped between the rectangular section 32 and the base 14 to grip the suture 46.

It is an important feature of the present invention that the packaging device 13 functions not only to maintain the T-fasteners in an orderly untangled configuration during sterilization, shipping and storage, but also functions as a means of facilitating the efficient loading of the T-fasteners in a slotted needle.

METHOD OF LOADING A T-FASTENER

With reference to FIGS. 6-9, the method of loading a T-fastener 19 in a slotted needle 18 will be illustrated. The slotted needle 18 is used in conjunction with a stylet 64. The stylet 64 is inserted into the second end 68 of the slotted needle 18 (commonly referred to as the "hub" of the needle) and used to push the T-fastener 19 from the slotted needle 18 and into a hollow organ within a patient. A first end 66 of the stylet 64 can be seen in FIG. 6. The first end 66 of the stylet contacts the "T" head 45 of the T-fastener 19. This is accomplished by the surgeon 53 applying pressure to the other end of the stylet 64 with a thumb or finger.

Figure 7:
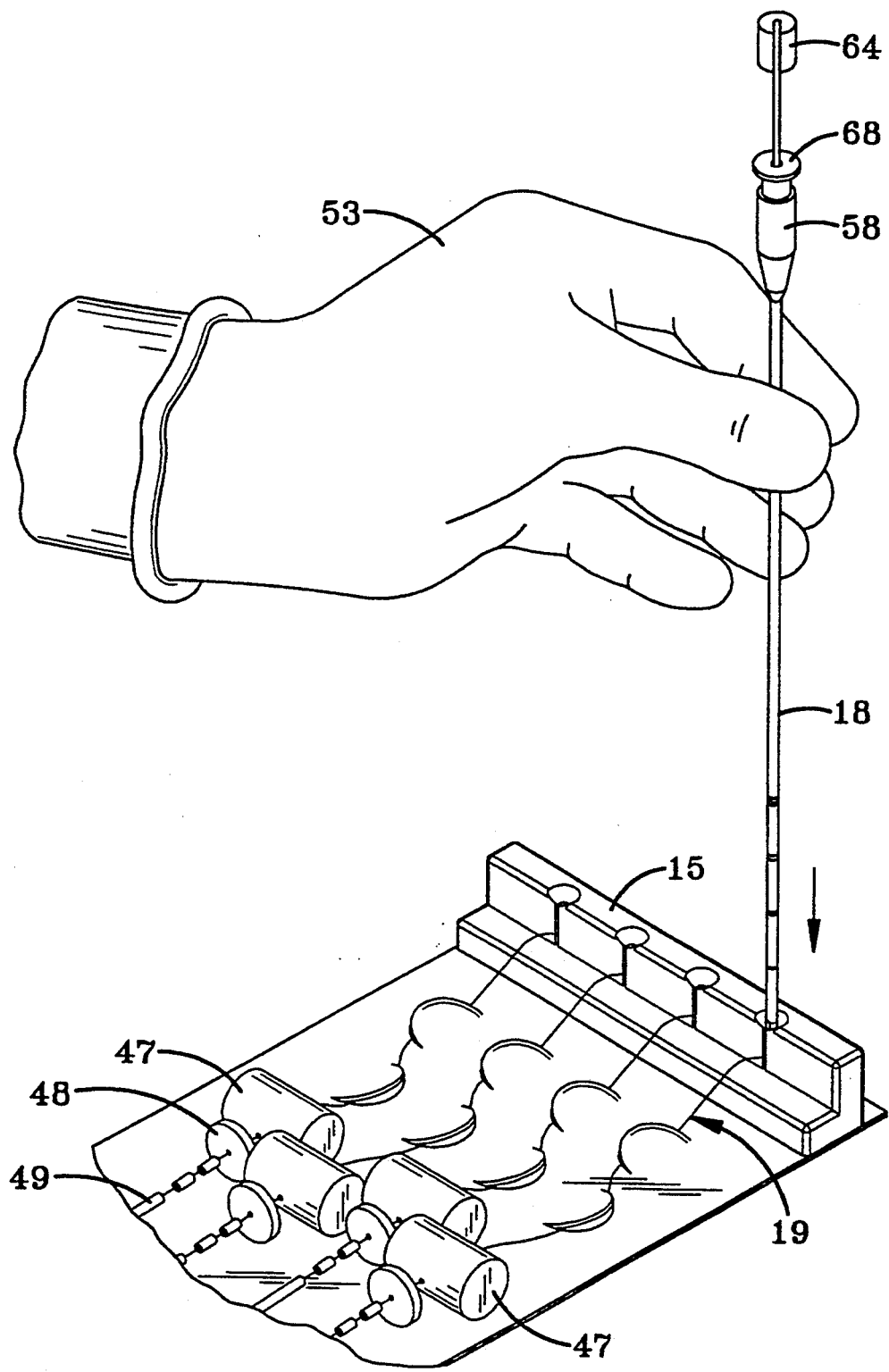
FIG. 7 illustrates a step in the procedure whereby the "T" head of a T-fastener can be loaded into the pointed end of a slotted needle.

With particular reference to FIGS. 6 and 7, the method of loading the T-fastener 19 into the slotted needle 18 will now be explained. With one hand the surgeon, or assistant, 53 grips the slotted needle 18 and lowers the sharpened end 56 of the slotted needle into a cylindrical recess 26 which contains the "T" head of a T-fastener. As can be best seen in FIG. 6, a longitudinally extending slot 70 in the sharp end 56 of the slotted needle 18 is aligned with the notch 38 in the housing 15 which communicates with the cylindrical recess 26. As such, the "T" head 45 of the T-fastener and the first end 50 of the suture 46 are received into the bore of the slotted needle 18. The inside diameter of the bore of the slotted needle 18 is slightly greater than the outside diameter of the "T" head 45 of the T-fastener 19 and the outside diameter of the slotted needle is slightly less than the inside diameter of the cylindrical recess 26. As such, the "T" head 45 of the T-fastener 19 can be received into the bore of the slotted needle 18, with the suture of the T-fastener extending through the longitudinal slot 70 in the needle.

Figure 8:
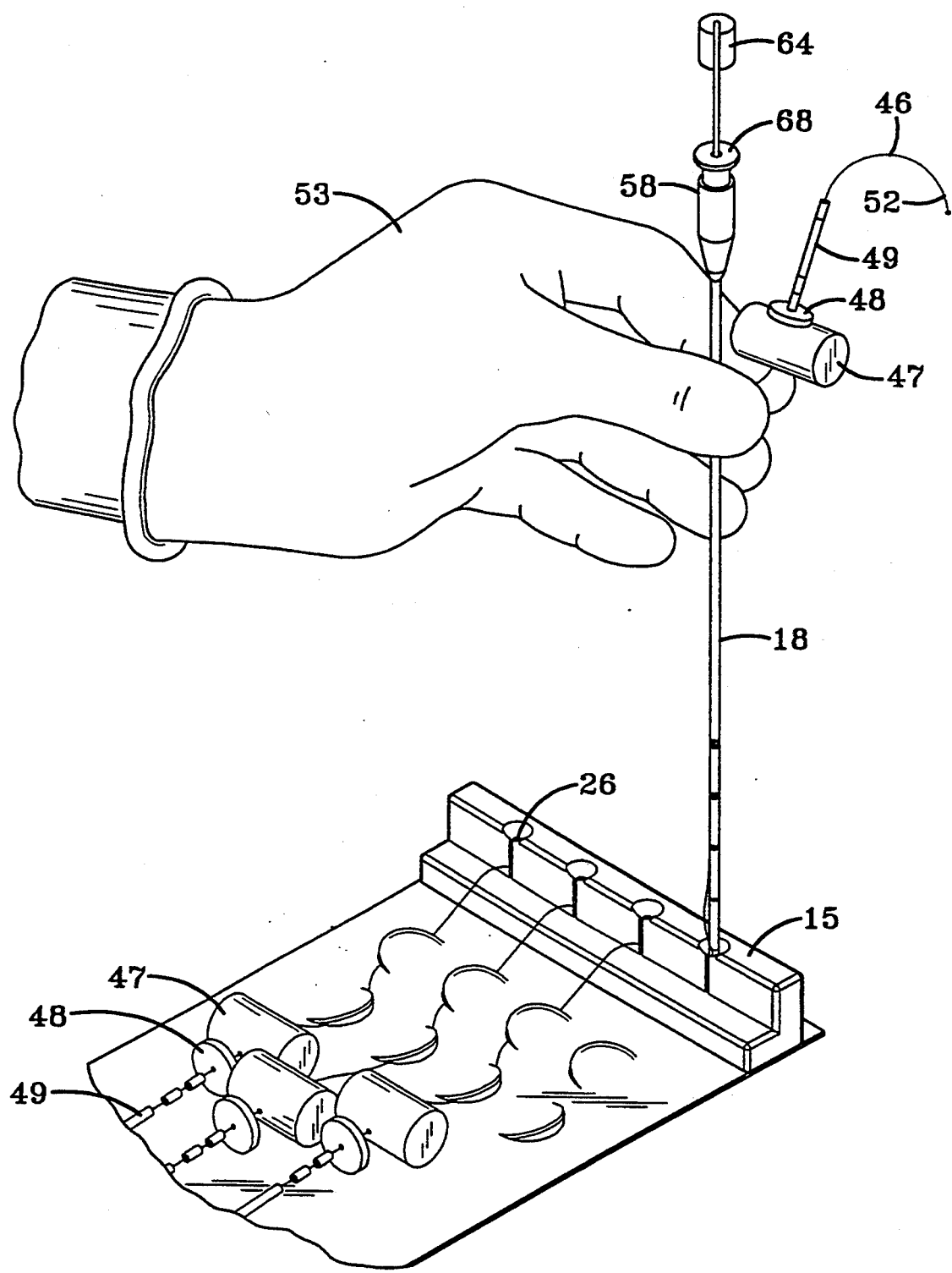
FIG. 8 illustrates a subsequent step of the procedure illustrated in FIG. 7.

With reference to FIG. 8, the next step of loading a T-fastener 19 into the slotted needle 18 is illustrated. With his other hand (the hand not gripping the slotted needle 18), the surgeon, or his assistant, 53 grips the second end 52 of the suture 46 and carefully removes the suture 46 from the cutouts 28 in the base 14 of the packaging device. After the suture 46 is free, the second end 52 of the suture 46 and other elements of the T-fastener 19 are lifted away from the base 14, the suture is extended along the exterior of the slotted needle and is gripped near the second end 68 of the slotted needle 18.

Figure 9:
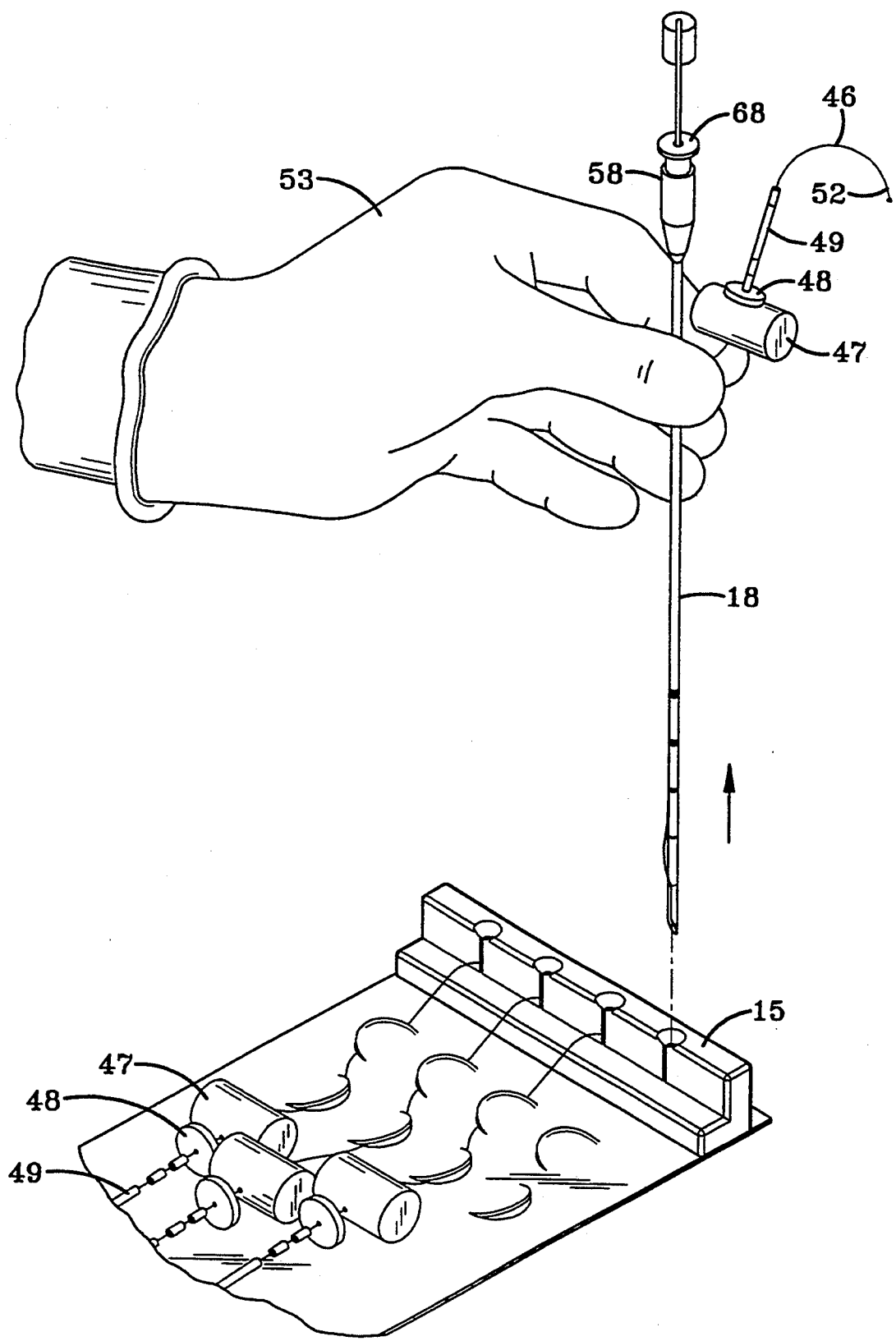
FIG. 9 illustrates a subsequent step of the procedure illustrated in FIGS. 7 and 8.

With reference to FIG. 9, the surgeon 53 then lifts the slotted needle 18 from the housing 15. With the T-fastener 19 loaded therein, ready for installation in the body of a patient.

The foregoing description is for purposes of illustration rather than limitation of the scope of protection of this invention. The latter is to be measured by the following claims, which should be interpreted as broadly as the invention permits.

We claim:

1. A method of loading a T-fastener into a slotted needle, said method comprising the steps of:
   (a) providing (i) a slotted needle having a bore therethrough and a longitudinally extending notch therein at a sharp end of the needle, and (ii) an assembly of a T-fastener and a device for loading a T-fastener into a needle, said T-fastener comprising a "T" head and a suture attached thereto, said device comprising a generally planar base and a housing attached thereto, said housing having a recess therein which contains the "T" head of the T-fastener, said recess having a longitudinal axis, a first end and a second end, the first end of said recess being open at a top surface of the housing and the second end of said recess being a solid surface of the housing, the longitudinal axis of the recess and the "T" head of the "T" fastener both being oriented generally vertically with respect to said base, said housing having a notch therein which communicates with said recess and is generally parallel to the longitudinal axis of said recess, the suture of said T-fastener extending through said notch and being secured to said generally planar base by means for securing; and
   (b) loading said T-fastener into said needle by sliding the sharp end of said needle into the recess in said housing and over said "T" head of said T-fastener, such that said "T" head is disposed within the bore of the needle and said suture extends through the slot in such needle, and placing tension on said suture and removing the needle and T-fastener from said recess.

* * * * *